(12) United States Patent
Reyes

(10) Patent No.: US 10,918,539 B1
(45) Date of Patent: Feb. 16, 2021

(54) GURNEY COMPRISING A MAGNETIC MEMBER FOR SECURING STRAPS

(71) Applicant: Billy Reyes, Compton, CA (US)

(72) Inventor: Billy Reyes, Compton, CA (US)

(*) Notice: Subject to any disclaimer, the term of this patent is extended or adjusted under 35 U.S.C. 154(b) by 85 days.

(21) Appl. No.: 16/210,360

(22) Filed: Dec. 5, 2018

(51) Int. Cl.
*A61G 1/044* (2006.01)
*A61G 1/02* (2006.01)
*A61G 1/056* (2006.01)
*A61F 5/37* (2006.01)

(52) U.S. Cl.
CPC ............ *A61G 1/044* (2013.01); *A61F 5/3776* (2013.01); *A44D 2203/00* (2013.01); *A61G 1/02* (2013.01); *A61G 1/0262* (2013.01); *A61G 1/0567* (2013.01)

(58) Field of Classification Search
CPC .......... A61G 7/012; A61G 13/06; A61G 1/02; A61G 1/04; A61G 1/044; A61G 1/052; A61G 1/0567; A61G 1/0212; A61G 1/0237; A61G 1/0262; A61G 1/0293
USPC .......... 5/628, 625, 81.1 R, 86.1, 611; 296/20
See application file for complete search history.

(56) References Cited

U.S. PATENT DOCUMENTS

| | | | | |
|---|---|---|---|---|
| 3,380,085 A | * | 4/1968 | Ferneau et al. | A61G 5/006 5/86.1 |
| 5,014,374 A | | 5/1991 | Williams | |
| 5,280,657 A | * | 1/1994 | Stagg | A47G 9/04 5/496 |
| 5,492,285 A | | 2/1996 | Hamrick | |
| 5,537,700 A | * | 7/1996 | Way | A61G 1/0567 296/20 |
| 5,575,026 A | * | 11/1996 | Way | A61G 1/0567 5/611 |
| 6,212,712 B1 | * | 4/2001 | Topp | A61G 1/04 5/509.1 |
| 6,276,010 B1 | * | 8/2001 | Way | A61G 1/0565 5/11 |
| 6,389,623 B1 | * | 5/2002 | Flynn | A61G 1/0567 296/20 |
| 6,526,611 B2 | * | 3/2003 | Flynn | A61G 1/0567 296/20 |
| 7,398,571 B2 | * | 7/2008 | Souke | A61G 1/0212 296/20 |
| 7,540,047 B2 | * | 6/2009 | Lambarth | A61G 1/0212 5/611 |
| 7,617,549 B2 | * | 11/2009 | Pollock | A61G 1/013 296/20 |

(Continued)

*Primary Examiner* — Robert G Santos
(74) *Attorney, Agent, or Firm* — Sanchelima & Associates, P.A.; Christian Sanchelima; Jesus Sanchelima

(57) ABSTRACT

A gurney comprising a magnetic member for securing straps is disclosed. The gurney comprises base members coupled to axle members. The gurney comprises support frame members coupled to the axle members. The gurney comprises a frame member coupled to the support frame members. The frame comprises a patient support. Further, the gurney comprises straps provided at either side of the frame member to secure a patient to the patient support. The straps comprise a male buckle member and a female buckle member. The gurney further comprises magnetic members coupled to the frame member. The male buckle member and the female buckle member are coupled to the magnetic members to secure the straps from falling down when the male buckle member and the female buckle member are not coupled or not in use.

8 Claims, 2 Drawing Sheets

(56) References Cited

U.S. PATENT DOCUMENTS

| | | | | |
|---|---|---|---|---|
| 7,694,368 B2 * | 4/2010 | Lewis, Jr. | ............ | A61G 1/0567 296/20 |
| 7,725,968 B2 * | 6/2010 | Lambarth | ................ | A61G 1/04 296/20 |
| 8,051,511 B2 * | 11/2011 | Nahavandi | ............ | A61G 1/0567 296/20 |
| 8,056,950 B2 * | 11/2011 | Souke | ...................... | A61G 1/04 296/20 |
| 8,677,530 B2 | 3/2014 | Calkin | | |
| RE44,884 E * | 5/2014 | Lambarth | ............ | A61G 1/0212 5/611 |
| 8,856,989 B2 * | 10/2014 | Lambarth | ............ | A61G 1/0567 296/20 |
| 10,080,693 B1 * | 9/2018 | Scheenstra | ............. | A61G 1/044 |
| 10,080,694 B1 * | 9/2018 | Scheenstra | ............... | A61G 1/04 |
| 10,335,328 B2 * | 7/2019 | Scheenstra | ............ | A61G 1/044 |
| 2002/0056162 A1 * | 5/2002 | Flynn | .................. | A61G 1/0262 5/611 |
| 2006/0075558 A1 * | 4/2006 | Lambarth | ........... | A61G 1/0293 5/611 |
| 2008/0028527 A1 * | 2/2008 | Lewis | .................. | A61G 1/0262 5/611 |
| 2008/0189860 A1 * | 8/2008 | Pollock | ................ | A61G 1/0262 5/611 |
| 2008/0211248 A1 * | 9/2008 | Lambarth | ............ | A61G 1/0293 296/20 |
| 2008/0276372 A1 * | 11/2008 | Lambarth | ............ | A61G 1/0237 5/611 |
| 2009/0178198 A1 * | 7/2009 | Nahavandi | ........... | A61G 1/0567 5/611 |
| 2009/0178200 A1 * | 7/2009 | Lambarth | ............ | A61G 7/0509 5/611 |
| 2010/0176618 A1 * | 7/2010 | Souke | .................. | A61G 7/0513 296/20 |
| 2019/0008707 A1 * | 1/2019 | Scheenstra | ............... | A61G 1/04 |
| 2020/0138648 A1 * | 5/2020 | Mansfield | ................ | A61G 1/02 |
| 2020/0268576 A1 * | 8/2020 | Scheenstra | ......... | A44B 11/2557 |

* cited by examiner

GURNEY COMPRISING A MAGNETIC MEMBER FOR SECURING STRAPS

BACKGROUND OF THE INVENTION

1. Field of the Invention

The present disclosure generally relates to a stretcher or gurney, which is used for moving patients. More particularly, the present disclosure relates to a gurney having a magnetic member provided at a frame to secure straps when the gurney is not in use.

2. Description of the Related Art

It is known that stretchers or gurneys are used for moving patients who require medical care. Typically, the gurneys are used by emergency medical services (EMS), military, and search and rescue personnel. Conventionally, a stretcher included a cot or litter, which was carried by two or more people for moving the patient. With improvements in the field of stretchers, the stretcher is provided with wheels, which makes it easier to move the patient from one place to another.

The gurneys are often equipped with different mechanisms, which allow adjusting the height of the stretchers and loading the patient onto an ambulance from the gurney and vice versa. Further, the gurneys are provided with straps for encircling the body of a patient at specific areas to secure the patient during transport.

Several examples of stretchers or gurneys are disclosed in the past. An example of a stretcher comprising straps is disclosed in a U.S. Pat. No. 5,014,374. In U.S. Pat. No. 5,014,374A, a restraint stretcher comprising an envelope for receiving a rigidifying backboard, and having transverse straps for encircling the body of a patient at specific areas, the straps being mounted for longitudinal movement to fit various sizes of patient.

Another example of a stretcher comprising straps is disclosed in a U.S. Pat. No. 8,677,530. In U.S. Pat. No. 8,677,530, a stretcher including a flexible base panel sized to support a person lying thereon during a rescue or extrication operation is disclosed. The base panel includes a header end and an opposite footer end, and further includes a head-supporting region and a body-supporting region. The head-supporting region is sized to support the head and shoulders of the person and the body-supporting region is sized to support a human torso. The stretcher further includes a securement strap extending from the head-supporting region along one side of the base panel and crossing over to the body-supporting region at the other side of the base panel. The securement strap extends diagonally across the shoulder and torso of the person to arrest the shoulder and limit sliding movement of the person toward the header end of the panel.

Although the straps disclosed in the above disclosures are effective in securing the patient during transport, they have few problems. For instance, when the straps are not in use, the straps may drop on the floor. This may be lead to several problems. For example, when the straps drop on floor, the straps may get contaminated. Further, the straps may get tangled in sidebars. Furthermore, the straps may get tangled in the wheels.

In order to overcome the above problems, a stretcher having retractable straps has been proposed in the past. One such example is disclosed in a U.S. Pat. No. 5,492,285.

In U.S. Pat. No. 5,492,285, a retractable strap apparatus for containing a strap that is commonly used on wheeled emergency tables and stretchers to secure a patient is disclosed. The strap is wound around a spring loaded retracting mechanism, which is contained within a cylindrical strap housing. The strap housing is mounted to a side of a wheeled emergency stretcher or table, and serves to contain the strap so as to prevent the strap from becoming entangled in a wheel of the stretcher or table.

Although the above disclosure solves the problem of securing the straps, the above disclosure too has few problems. For instance, the retractable strap apparatus uses a spring loaded retracting mechanism for wounding the strap. Over a period of time, the spring loaded retracting mechanism may not work properly. Further, the spring loaded retracting mechanism needs to be affixed to the stretcher at the time of manufacturing. In case the spring loaded retracting mechanism fails, then the strap may not be usable to secure the patient. As a result, the stretcher becomes unusable.

Other documents describing the closest subject matter provide for a number of more or less complicated features that fail to solve the problem in an efficient and economical way. None of these patents suggest the novel features of the present invention. Specifically, none of the disclosures in the art disclose a gurney having a magnetic member provided at a frame in proximity to straps, such that the straps can be coupled to the magnetic member when the straps are not in use.

Therefore, there is a need in the art for a gurney having a magnetic member provided at a frame in proximity to strap to couple the strap to the magnetic member when the strap is not in use.

SUMMARY OF THE INVENTION

It is one of the main objects of the present invention to provide a gurney comprising a magnetic member for securing straps and that avoids the drawbacks of the prior art.

It is one object of the present invention to provide a gurney comprising a magnetic member for securing straps. The gurney comprises base members coupled to axle members. The gurney comprises support frame members coupled to the axle members. The gurney comprises a frame member coupled to the support frame members. The frame comprises a patient support. Further, the gurney comprises straps provided at either side of the frame member to secure a patient to the patient support. The straps comprise a male buckle member and a female buckle member. The gurney further comprises magnetic members coupled to the frame member. The male buckle member and the female buckle member are coupled to the magnetic members to secure the straps from falling down when the male buckle member and the female buckle member are not coupled or not in use.

It is one object of the present invention to provide the magnetic member in proximity to the straps such that buckles of the strap can be coupled to the magnetic member when the straps are not in use.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which.

DETAILED DESCRIPTION OF THE EMBODIMENTS OF THE INVENTION

The following detailed description is intended to provide example implementations to one of ordinary skill in the art, and is not intended to limit the invention to the explicit disclosure, as one or ordinary skill in the art will understand that variations can be substituted that are within the scope of the invention as described.

The present disclosure discloses a gurney comprising a magnetic member for securing straps. The gurney comprises base members coupled to axle members. The gurney comprises support frame members coupled to the axle members. The gurney comprises a frame member coupled to the support frame members. The frame comprises a patient support. Further, the gurney comprises straps provided at either side of the frame member to secure a patient to the patient support. The straps comprise a male buckle member and a female buckle member. The gurney further comprises magnetic members coupled to the frame member. The male buckle member and the female buckle member are coupled to the magnetic members to secure the straps from falling down when the male buckle member and the female buckle member are not coupled or not in use.

Figure 1:
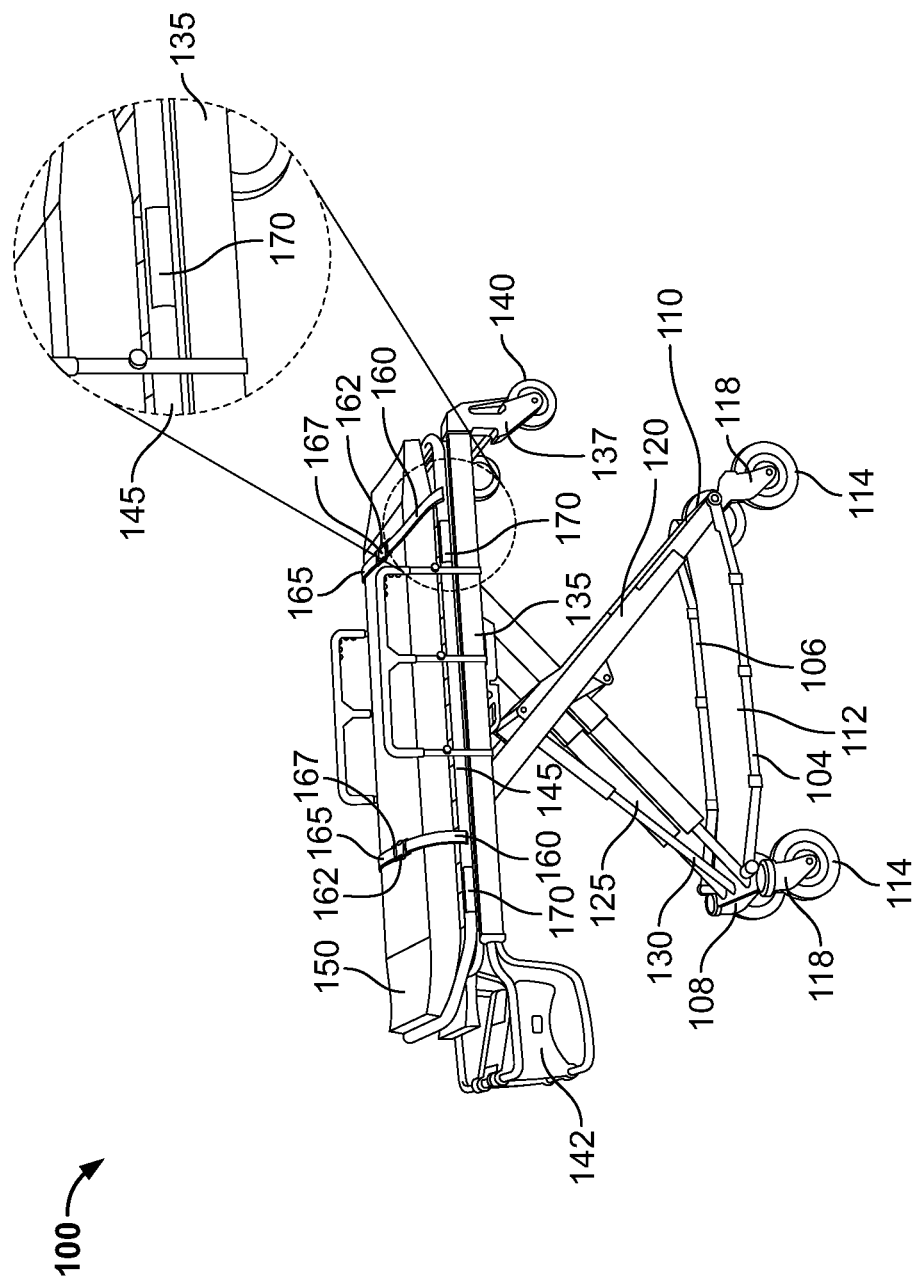
FIG. 1 illustrates a perspective view of a gurney 100 having straps 160 and a magnetic member 170, in accordance with one embodiment of the present disclosure.
Figure 2:
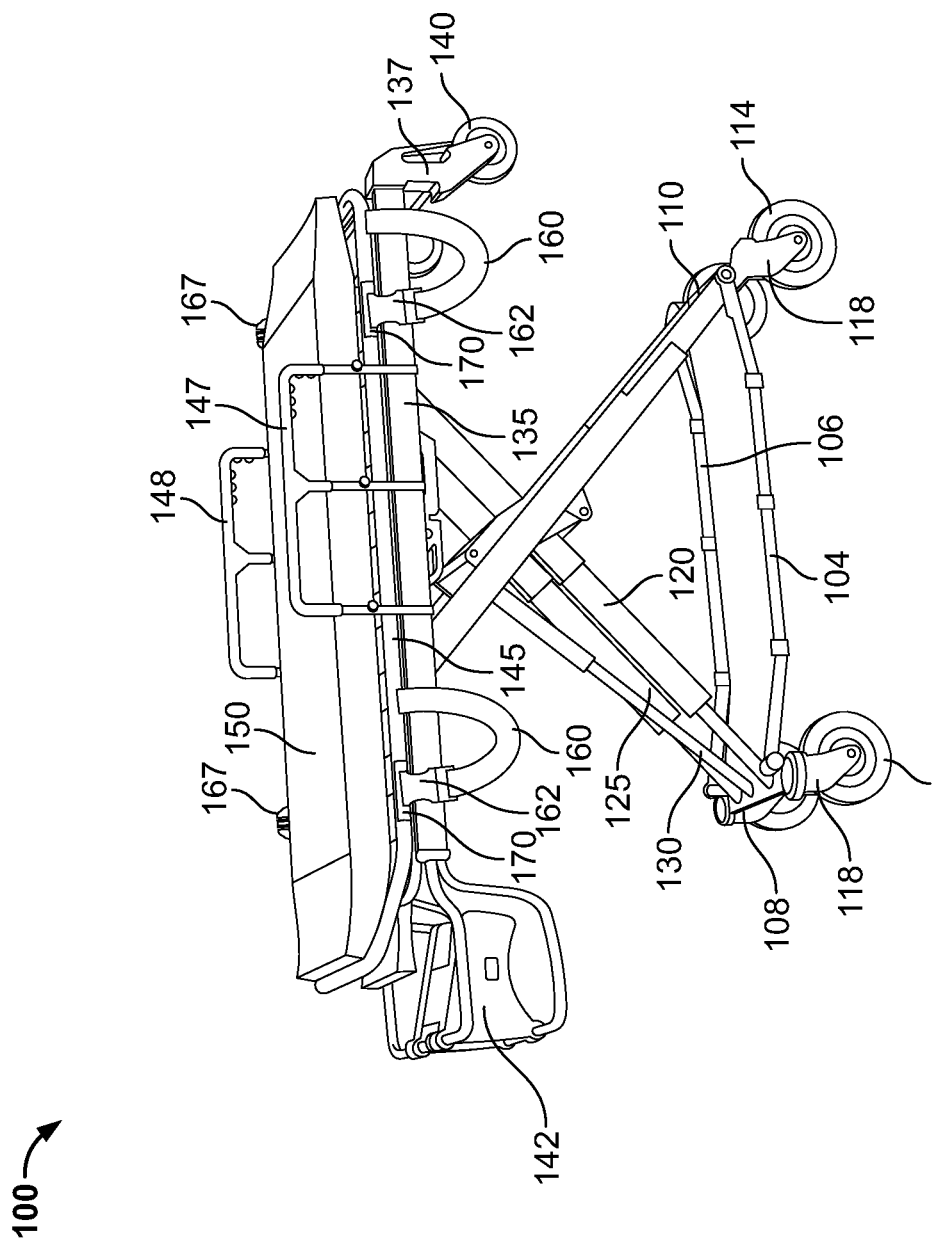
FIG. 2 illustrates a buckle of the strap 160 coupled to the magnetic member 170, in accordance with one embodiment of the present disclosure.

Various features and embodiments of a gurney comprising a magnetic member for securing straps are explained in conjunction with the description of FIGS. 1-2.

Referring to FIG. 1, a perspective view of a gurney 100 is shown, in accordance with one embodiment of the present disclosure. The gurney 100 comprises a first base member 104 and a second base member 106. The first base member 104 and the second base member 106 are placed parallel to each other.

The first base member 104 and the second base member 106 are coupled using a first axle member 108 at one end. Further, the first base member 104 and the second base member 106 are coupled using a second axle member 110 at another end. The first base member 104 and the second base member 106 are provided with a sheet 112. The sheet 112 may be used for storing dressing, other medical equipment etc. At the ends of the first axle member 108 and the second axle member 110, wheels 114 are provided which help in maneuvering the gurney 100. As can be seen, the wheels 114 are coupled to the ends of the first axle member 108 and the second axle member 110 using brackets 118.

The gurney 100 is provided with a first scissor frame member 120 and a second frame member 125. It should be understood that the first scissor frame member 120 and the second frame member 125 are provided in parallel to each other and coupled at the ends of the first axle member 108 and the second axle member 110. Further, the gurney 100 comprises an elevation assist member 130, which helps to raise or lower the first scissor frame member 120 and the second frame member 125.

The first scissor frame member 120 and the second frame member 125 are coupled to a lower frame member 135. Each of the first scissor frame member 120 and the second frame member 125 are coupled to the lower frame member 135 using known mechanisms such as welding, fastening and other known mechanisms. At one end, the lower frame member 135 comprises brackets 137 which are fixedly secured to the lower frame member 135. Each of the brackets 137 rotatably supports a respective loading wheel 140. The loading wheels 140 facilitate insertion of the gurney 100 into an emergency vehicle (not shown). The lower frame member 135 comprises a housing 142 at other end for placing components required to treat the patient or to use the housing 142 to maneuver the gurney 100.

The lower frame member 135 further comprises an upper frame member 145. The upper frame member 145 is a tubular frame. The upper frame member 145 is provided with a first collapsible side rail 147 and a second collapsible side rail 148. The gurney 100 further comprises a patient support 150. The patient support 150 may indicate a flat surface such as mattress, which is rigid. The patient support 150 may be coupled to the center portion of the lower frame member 135. It should be understood that the first collapsible side rail 147 and the second collapsible side rail 148 may be selectively operated to receive patient or to adjust position of the patient on the patient support 150.

As in conventional gurneys, the gurney 100 comprises straps i.e., a first strap 160 and a second strap 165, each coupled to the upper frame member 145 at opposite sides. The first strap 160 comprises a male buckle member 162. The second strap 165 comprises a female buckle member 167. In order to couple the first strap 160 and the second strap 165, the male buckle member 162 and the female buckle member 167 are coupled as shown in FIG. 1.

In accordance with one embodiment of the present disclosure, the upper frame member 145 is provided with a magnetic member 170. The magnetic member 170 may be placed in proximity to the straps 160, 165 provided at the upper frame member 145. In one example, the magnetic members 170 may be removably coupled to the upper frame member 145. Specifically, the magnetic members 170 are coupled to the upper frame member 145 in proximity to the straps 160, 165.

FIG. 1 illustrates the first strap 160 coupled to the second strap 165. Specifically, the male buckle member 162 is coupled to the female buckle member 167. In one example, the male buckle member 162 is coupled to the female buckle member 167 to secure the straps 160, 165 from falling on ground when not in use. In another example, the male buckle member 162 is coupled to the female buckle member 167 to secure a patient (not shown) to the patient support 150 during transport.

When the straps 160, 165 are not in use, i.e., the male buckle member 162 is not coupled to the female buckle member 167, the first strap 160 and the second strap 165 may be coupled to the magnetic member 170 provided at the upper frame member 145. Specifically, the male buckle member 162 of the first strap 160 is coupled to the magnetic member 170 at one side. Similarly, the female buckle member 167 of the second strap 165 is coupled to the magnetic member 170 at another or opposite side, as shown in FIG. 2.

It should be understood that the number of magnetic members 170 provided at upper frame member 145 might be equal to or more than the number of straps provided at the upper frame member 145. Further, it should be understood that the magnetic members 170 are provided in proximity to the straps 160, 165 such that it will be easy to couple the male buckle member 162 and the female buckle member 167 to the magnetic members 170 when not in use i.e., when the straps are not used to secure the patient.

Based on the above, it is evident that whenever a user such as medical personnel or rescue personnel removes the straps to free the patient from the patient support, the user may attach the male buckle member and the female buckle member of the straps to the magnetic member provided in proximity such that the straps are secured to the magnetic member. As the straps are secured to the magnetic member when not in use, the straps falling on ground and getting contaminated is prevented. Further, the straps becoming tangled in the scissor frame members or wheels or other component of gurney is prevented.

Further, it should be understood that the magnetic members may be provided at equal distance from one another or may be provided at varied distance from one another. The position of the magnetic members may depend on the position of the straps at the lower frame member.

Based on the above, it is evident that the user may couple the buckle of the straps to the magnetic member to prevent the straps from falling on ground or getting entangled in bars or wheels.

It should be understood that the magnetic member disclosed herein can be affixed to an existing gurney or may be provided along with a new gurney. If the user wishes to change the position of the magnetic member at the lower frame member or at the upper frame member, he can simply remove the magnetic member and affix in proximity to the straps.

It is to be noted that the drawings shown herein are provided for illustrative purpose only. However, a person skilled in the art will appreciate that other gurneys, which have different mechanisms to adjust the height, and have different shape, and structure for securing the patient using the straps can be fitted with the magnetic member described herein to secure the straps when not in use.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A gurney comprising:
   base members coupled to axle members;
   support frame members coupled to the axle members;
   a frame member coupled to the support frame members, wherein the gurney comprises a patient support, wherein said frame member includes a lower frame member and an upper frame member, wherein said lower frame member includes a first end and a second end, wherein said lower frame member includes lower frame brackets at said first end, wherein said lower frame member includes a housing located at said second end, wherein said upper frame member is a tubular frame member;
   straps provided at either side of the frame member to secure a patient to the patient support, wherein the straps comprise a male buckle member and a female buckle member; and
   magnetic members coupled to the upper frame member, said upper frame member including a first side and a second side, wherein a first magnetic member having a rectangular shape is removably coupled to an outer surface of said first side, wherein a second magnetic member having a rectangular shape is removably coupled to an outer surface of said second side, wherein the male buckle member and the female buckle member are coupled to the magnetic members to secure the straps from falling down when the male buckle member and the female buckle member are not coupled or not in use.

2. The gurney of claim 1, wherein the gurney comprises wheels provided beneath the axle members to maneuver the gurney.

3. The gurney of claim 1, wherein the straps are coupled to the upper frame member.

4. The gurney of claim 1 wherein said base members include a sheet located therebetween adapted to hold clothing.

5. The gurney of claim 1 wherein said lower frame brackets include loading wheels mounted thereon.

6. The gurney of claim 1 wherein said upper frame member includes a first collapsible side rail and a second collapsible side rail.

7. The gurney of claim 1 wherein said gurney includes an elevation assist member adapted to help raise or lower said support frame members.

8. A gurney, comprising:
   a) a first base member and a second base member, wherein said first base member and said second member are placed parallel to each other, said first base member and said second base member being coupled through a first axle member at a first end, said first base member and said second base member being coupled through a second axle member at a second end, a sheet located between said first base member and said second base member, wherein said sheet is adapted to store dressing and medical equipment, wherein said first axle member and said second axle members includes brackets at each end, wheels being coupled to said brackets;
   b) a first scissor frame member and a second scissor frame member being parallel to each other and coupled at ends of said first axle member and said second axle member, wherein said gurney further includes an elevation assist member adapted to help raise and lower said first scissor frame member and said second scissor frame member;
   c) a lower frame member coupled to said first scissor frame member and said second scissor frame member, wherein said lower frame member includes lower frame brackets fixedly secured to a first end of said lower frame member, wherein said lower frame brackets includes loading wheels attached thereon, wherein a second end of said lower frame member includes a housing adapted for placing components for treating a patient;
   d) an upper frame member mounted on top of said lower frame member, wherein said upper frame member is a tubular frame, wherein said upper frame member includes a first collapsible side rail and a second collapsible side rail, wherein said gurney further includes a patient support being a flat mattress mounted to a top end of said upper frame member;
   e) a first strap and a second strap coupled to said upper frame member at opposite sides, wherein said first strap includes a male buckle member, wherein said second strap includes a female buckle member;
   f) a first magnetic member and a second magnetic member removably coupled to said upper frame member, wherein said upper frame member includes a first side and a second side, said first magnetic member having a rectangular shape and coupled to an outer surface of said first side of said upper frame member, wherein said second magnetic member has a rectangular shape and is coupled to an outer surface of said second side of said upper frame member, wherein said male buckle member of said first strap is coupled to said first magnetic member, wherein said female buckle member of said second strap is coupled to said second magnetic member.

* * * * *